(12) United States Patent
Reybrouck et al.

(10) Patent No.: US 10,136,966 B2
(45) Date of Patent: Nov. 27, 2018

(54) ORTHODONTIC APPLIANCE

(71) Applicant: Dentbend BVBA, Liederkerke (BE)

(72) Inventors: Koenraad Gerald Rijkaard Lode Reybrouck, Etterbeek (BE); Wouter Gerald Herman Rik Reybrouck, Liedekerke (BE); Isabelle Diane Savoye, Liedekerke (BE)

(73) Assignee: Dentbend BVBA, Liederkerke (BE)

( * ) Notice: Subject to any disclaimer, the term of this patent is extended or adjusted under 35 U.S.C. 154(b) by 0 days.

(21) Appl. No.: 14/917,150

(22) PCT Filed: Sep. 5, 2014

(86) PCT No.: PCT/EP2014/068985
§ 371 (c)(1),
(2) Date: Mar. 7, 2016

(87) PCT Pub. No.: WO2015/032918
PCT Pub. Date: Mar. 12, 2015

(65) Prior Publication Data
US 2016/0206405 A1    Jul. 21, 2016

(30) Foreign Application Priority Data

Sep. 5, 2013   (NL) ..................................... 2011385

(51) Int. Cl.
*A61C 7/28* (2006.01)
*A61C 7/12* (2006.01)
*A61C 7/14* (2006.01)
*A61C 7/20* (2006.01)
*A61C 7/22* (2006.01)

(52) U.S. Cl.
CPC ................ *A61C 7/287* (2013.01); *A61C 7/12* (2013.01); *A61C 7/14* (2013.01); *A61C 7/145* (2013.01); *A61C 7/20* (2013.01); *A61C 7/22* (2013.01); *A61C 7/28* (2013.01)

(58) Field of Classification Search
CPC ........... A61C 7/287; A61C 7/145; A61C 7/12; A61C 7/28; A61C 7/22; A61C 7/14; A61C 7/20
See application file for complete search history.

(56) References Cited

U.S. PATENT DOCUMENTS

| | | | | |
|---|---|---|---|---|
| 3,052,027 A | * | 9/1962 | Wallshein | A61C 7/12 433/11 |
| 3,505,736 A | | 4/1970 | Brader et al. | |
| 4,512,740 A | * | 4/1985 | Kurz | A61C 7/12 433/22 |

(Continued)

FOREIGN PATENT DOCUMENTS

| EP | 1405610 A2 | 4/2004 |
|---|---|---|
| WO | 2009126433 A2 | 10/2009 |

(Continued)

*Primary Examiner* — Nicholas Lucchesi
*Assistant Examiner* — Shannel Wright
(74) *Attorney, Agent, or Firm* — The Webb Law Firm

(57) ABSTRACT

The appliance includes a body that snaps onto the brackets attached to teeth with latching slots and so becomes detachable for daily cleaning by the patient. Inside the body there is an integrated spring function. The fabrication of the polymeric body can be done by 3D printing, which makes it possible to print integrated spring elements connecting the latching slots with the body.

19 Claims, 9 Drawing Sheets

(56) References Cited

U.S. PATENT DOCUMENTS

| | | | | |
|---|---|---|---|---|
| 4,597,739 | A * | 7/1986 | Rosenberg | A61C 7/12 433/16 |
| 4,867,678 | A * | 9/1989 | Parker | A61C 7/12 433/8 |
| 4,902,224 | A * | 2/1990 | Collins | A61C 7/12 433/8 |
| 5,820,368 | A * | 10/1998 | Wolk | A61C 7/02 433/141 |
| 6,264,468 | B1 * | 7/2001 | Takemoto | A61C 7/12 433/10 |
| 7,306,458 | B1 * | 12/2007 | Lu | A61C 7/14 433/16 |
| 2004/0067463 | A1 * | 4/2004 | Rosenberg | A61C 7/12 433/6 |
| 2005/0003319 | A1 * | 1/2005 | Kuo | A61C 7/08 433/6 |
| 2005/0277084 | A1 * | 12/2005 | Cinader | A61C 7/20 433/20 |
| 2005/0277089 | A1 * | 12/2005 | Brajnovic | A61C 13/275 433/167 |
| 2006/0093984 | A1 * | 5/2006 | Rosenberg | A61C 7/12 433/6 |
| 2009/0215003 | A1 * | 8/2009 | Swain | A61C 7/00 433/24 |
| 2010/0239992 | A1 * | 9/2010 | Brandt | A61C 7/08 433/6 |
| 2011/0027743 | A1 * | 2/2011 | Cinader, Jr. | A61C 7/10 433/11 |
| 2011/0311935 | A1 * | 12/2011 | Dumas | A61C 7/14 433/16 |
| 2012/0270174 | A1 * | 10/2012 | Meley | A61C 7/12 433/11 |
| 2013/0125398 | A1 * | 5/2013 | Curiel | A61C 7/12 29/896.1 |
| 2014/0335468 | A1 * | 11/2014 | Dickerson | A61C 7/36 433/19 |
| 2017/0105817 | A1 * | 4/2017 | Chun | A61C 7/12 |

FOREIGN PATENT DOCUMENTS

| | | |
|---|---|---|
| WO | 2011036249 A1 | 3/2011 |
| WO | 2011067510 A1 | 6/2011 |

* cited by examiner

ORTHODONTIC APPLIANCE

CROSS-REFERENCE TO RELATED APPLICATIONS

This application is the United States national phase of International Application No. PCT/EP2014/068985 filed Sep. 5, 2014, and claims priority to Netherlands Patent Application No. 2011385 filed Sep. 5, 2013, the disclosures of which are hereby incorporated in their entirety by reference.

FIELD OF THE INVENTION

The invention relates to an orthodontic appliance comprising at least one bracket comprising a base for connection to a surface of a tooth, which appliance further comprises a body, which is, in use, coupled to each of said at least one brackets.

The invention further relates to components of such orthodontic appliance and the use thereof.

BACKGROUND OF THE INVENTION

Orthodontic appliances are available in different kinds. Some appliances are designed for children and youth, and serve the influence the growth of the jaw. They are for instance known as a splint and as a trainer. Other appliances serve to displace individual teeth, relative to neighbouring teeth. These appliances are, in most cases, characterised by the presence of brackets located on the individual teeth. The brackets are typically coupled by means of a wire member, which will put a force on a tooth that is displaced and to be shifted relative to neighbouring teeth. In dependence of the stage of treatment, the material and thickness of the wire member is chosen by an orthodontist. The treatment therein usually starts with a wire member that exerts a small force on the teeth. This small force reduces as the teeth displace over time under its influence. Subsequently, normally once the force becomes too small to further displace the teeth, the wire member is exchanged. Generally, a thicker wire member is inserted, which results therein that the force acting on the teeth will become again higher.

Moreover, the wire member is tuned to one or more individual teeth. This tuning is also known as activation. In this activation process, an orthodontist modified the shape of the wire member locally, to obtain a desired moment of force. Herein, the desired moment of force not merely is characterised through its magnitude (for which the material and size of the wire member is primarily responsible) but also the orientation. The moment of force may be exerted in 6 dimensions: along the three carthesian axes, and according to three rotational orientations. While in the following reference will be made to 'force', the skilled person will understand that 'force or moment of force' is actually a more accurate reference.

This well-known type of orthodontic appliances has the difficulty of a precise force setting as a disadvantage. The skill of the orthodontist defines the force exerted on the teeth. But the wire member is subject to unintended deformation in the course of use. Moreover, which is often quite problematic, the wire member will exert a force on a misplaced tooth, but also a counterforce on neighbouring teeth. This counterforce may well be undesirable, in that a correctly positioned tooth is made subject to a force into a certain direction. As a consequence, such tooth may get a displacement, with all complications thereof.

An appliance proposal is disclosed in WO2009/126433A1, which tries to solve these problems by exerting forces on individual teeth by means of separate force exertion means for each tooth. The disclosed appliance comprises a polymeric body shaped in accordance with the jaw. Individual wire members are locked into said polymeric body and extend out of said body towards individual brackets on individual teeth. The wire members optionally comprise flexible springs allowing for longitudinal movement (i.e. in a direction generally along the direction of extension of the wire members away from the polymeric body). Therewith tensile or compressive forces in the longitudinal direction can be achieved. Herewith, both intrusive and extrusive forces could be applied on the teeth. The individual wire members are coupled to the brackets, particularly via magnetic couplings, and on the basis of a first and second coupling with complementary shapes.

However, the wire members of the disclosed appliance appear even more sensitive to deformation than the wire member of the existing appliances running along the teeth. This sensitivity is even more enhanced in that the polymeric body with the wire members is removable. When putting the removable section back into the mouth, all individual wire members require coupling with corresponding brackets. If some of the wire members are rather flexible and do not fit immediately, a user could easily deform some of those wire members. Moreover, the wire members run the risk of deformation under a cleaning operation with for instance a tooth brush.

It is already for this reason not surprising that the disclosed appliance is not known, i.e. the disclosed appliance appears an idea, but is not recognized as a commercially feasible product.

A further proposal for an appliance is known from WO2011/036249A1. The known appliance comprises an orthodontic working arch wire for moving at least one tooth of a dental arch of a patient to be treated from a first spatial configuration to a second spatial configuration, including an element for connecting to the tooth to be treated, which is intended to be attached onto the tooth being treated by snap-fitting onto a bracket glued onto one of the surfaces of said tooth. The working arch wire is rigid and the connecting element is movable relative to the orthodontic working arch wire by elastically deformable connecting means. The dental arch or body would be replaced in subsequent stages of the treatment, so as to redefine the force on the tooth or teeth. However, specific channels are deemed necessary for clipping a tool needed to position the body in the patient's mouth. That looks awkward in practice.

SUMMARY OF THE INVENTION

It is therefore an object of the invention to provide an improved appliance which allows for individually addressing mal positioned teeth without providing a substantial counterforce on neighbouring teeth and which is less sensitive for deformation during use compared with the disclosed appliance, and which may be adequately positioned into the mouth without too much problems.

It is another object to provide a manufacturing method for such appliance.

It is a further object to provide a computer aided design method and a computer aided design system for at least a connection element within the appliance It is a further object to provide an orthodontic treatment method.

This first object is achieved in an orthodontic appliance comprising at least one bracket, each bracket having a base for attachment to a surface of a tooth, which appliance further comprises a body, which is, in use, coupled to each of said at least one bracket, wherein the body is provided with at least one connection element that in use cooperates with said at least one bracket to form a connection and that is arranged on said body, wherein the connection element comprising a slot and the bracket comprises a locking element for insertion into said slot, which locking element and slot are locking means configured for removably connecting the body and the bracket via the connection element, wherein the bracket is provided with a stem, such that the connection element generates a force onto a respective tooth via said stem, which the locking element has a larger diameter than the stem.

The said other object is achieved in a method of manufacturing a component for use in said appliance, comprising the steps of: (1) Defining a force with its orientation to be applied to a tooth; (2) Defining a model wherein a property of a connection element is optimized in view of the defined force to be applied on the respective tooth; and (3) Generating said component conforming to said model.

The further object is achieved in a method of orthodontic treatment, comprising: attaching at least one bracket to a surface of a respective tooth; providing a component of the invention, and connecting the connecting element of said component to a respective bracket under movement of the component, generally in a substantially gingival direction.

In accordance with the invention, said wire members are replaced with connection elements which are arranged on the body. Therewith, there is a spatial continuity from the body via said connection element and the bracket to the tooth. The ease of modification of wire members will no longer be possible, but this can be replaced by means of prototyping and particularly printing techniques. The major advantage thereof for the orthodontic treatment, is that such renewed manufacture of the unit may start from the model, which is based on optical detection and investigation of the teeth. The model is also typically available in digital form. Thus the current manual activation carried out by an orthodontist by means of modification of the wire member can be replaced by a digital activation, derived from inspection; i.e. a computer program may calculate needed forces and the orientation thereof in six dimensions. These may then be converted into recipe for the manufacturing of a new unit. If needed, such recipe may be steered by the orthodontist; for instance the magnitude of the force could be set in the course of the orthodontic treatment on the basis of visual inspection and experience.

The use of connection elements forming part of the body has the benefit that this is in use a single, uninterrupted unit. It means that the unit can be designed as a whole. The force on the tooth is in the invention particularly defined by means of the connection element, which may be or may comprise a structure that is flexible relative to the body.

It is an advantage of the present invention that its use is not limited to the inner side of the tooth, but can also be applied on the outer side. It is a further advantage, that the invention is not merely feasible to displace a single tooth, but also to correct positions of two adjacent teeth.

The connection element is suitably designed to exert the predefined force on a respective tooth. The body with the at least one connection element is more particularly designed such that a elastic deformation occurs in the connection element upon connection of the connection elements to the brackets. This deformation results, in the connection element, in a spring-like reaction force onto the tooth.

Particularly, the design is made such that the connection element elastically deforms upon insertion, for instance in accordance with an elastic mode. This deformed connection element will act as a spring, desirous of returning to its original, undeformed state, and therewith exerting the force on the tooth. Normally, when the tooth has been displaced in the intended direction, the deformation of the connection element, and thus the related reaction force, becomes smaller.

In accordance with the invention, the connection between the at least one bracket and the connection element is a removable connection. This has not merely the advantage of better cleaning, but it further allows the preparation of the brackets by means of another process than the connection element and/or the body. Particularly, the brackets may be designed to be standardized for a specific size and type of tooth, and then be produced at large scale to reduce cost price. Furthermore the brackets may be designed in one or more materials different from those of the connection elements. Therewith adhesion to the teeth may be improved, and durability may be increased. Suitable materials for the bracket are for instance metals, ceramics, such as zirconia-based ceramics or alternatively composites and polymers. It will be understood that generally a plurality of brackets will be available. The number thereof is suitably equal to the number of teeth. It is however not excluded in the invention that the number of brackets is smaller than the number of teeth.

Particularly, the connection element is coupled to the bracket by means of locking means, wherein a first and a second locking feature are complementarily shaped, and wherein a first locking feature defines a slot and a second locking feature is defined for insertion into said slot. The slot will limit movement of the inserted locking feature. Typically, merely one path in preferably a single direction will remain through which insertion and removal can take place. Therewith, play in other direction may be minimized, resulting in an excellent force transmission from the connection element onto the bracket. The slot is defined in the connection element, and the feature for insertion into the slot is defined on the bracket. The bracket is provided with a stem protruding from the base. The stem can be used to increase a distance between the body and the teeth. This appears most user-friendly, both for the removal and insertion process, but also for the cleaning of the slotted part. Moreover, the distance between the tooth and connection element allows the connection element to be arranged around the locking element on effectively all sides. This provides a good and stable connection. Moreover, in this way, the patient may himself insert the body. Particularly, he may fix the locking elements into the slots of the connection element essentially one-by-one, which is highly convenient.

In one implementation hereof, the connection element comprises a deformable bridge to said body, which bridge may be deformed upon connecting of the bracket to said locking feature, therewith generating said force on said tooth.

More preferably, the slot is defined as a latching slot, so that the inserted element is locked within the slot.

Moreover, the stem may be used in combination with a position of the body that is at least partially shifted relative to a plane of the teeth. This is deemed particularly preferable, if the body is attached on the lingual side of the teeth or at the palatal side. Therewith, various placement options for the body are available. An orthodontic practitioner may then choose a location most suitable for the treatment and causes the patient least irritation. Such irritation may be, for instance, an irritation of the tongue and/or difficulties with speaking. It is believed that such disadvantages will generally be reduced, dependent on the patient, when the body is located in a shifted position, more to the upper side or the lower side of the mouth.

Preferably, the locking feature of the bracket resides on the stem and has a larger diameter than the stem, when seen in perpendicular projection on the base. The locking feature may then be encapsulated on all sides. Furthermore, if the distance between base and locking feature is too short, there may be a risk of insufficient hygiene due to food sticking into a groove between the two.

Preferably, the connection element is provided with an end stop or protection device. Such end stop has the effect of absorbing a large sudden force exerted on the body typically resulting from biting. Such large force could otherwise damage the appliance, for instance as a fracture and/or deformation of the connection element or by removal of one or more brackets from the surfaces of the corresponding teeth. The needed absorption is, in a particular implementation, realized in that the force is distributed over the full surface of the slot. Furthermore, a connection between the body and the connection element may be provided with an overload device, for instance having compressive means. Such compressive means would particularly absorb forces exceeding a certain threshold value. For instance, the means may be in the form of a structured material or a material comprising a first phase and a second phase.

Preferably, the deformable bridge (or any other deformable portion of the connection element and/or the body) is defined by means of the use of specific materials, such as flexible materials, more preferably elastic materials. Elastic materials are known per se, and include elastomers, silicones, plastics, nylon, latex, balata, but also foam-type materials, such as a polyethylene foam.

In accordance with the preferred manufacturing process, different materials may be applied adjacent to each other (i.e. within a single plane), for instance in a printing process. This allows that the deformable materials may be structured in accordance with a predefined (three-dimensional) structure. Therewith the orientation of the force can be specified in a precise manner. In one suitable or alternative embodiment, the deformable material could be contained within an encapsulation that is prone to conditions occurring in the mouth.

The unit may be manufactured as a whole in a single manufacturing process. Furthermore, the unit may contain a first pre-manufactured part, more specifically the body or a large portion thereof, and a second part—particularly the connection element—manufactured in situ. The first part herein acts as a substrate for the second part, which is for instance made by means of printing. Both these options result in a monolithic unit.

Alternatively, the manufacturing of the unit may comprise an assembly step. In this embodiment, the unit comprises a first part and a second part complementary to the first part, which parts can be assembled to each other. The assembly will occur as part of the manufacturing process, i.e. in a laboratory, particularly of an orthodontic practitioner. In case of such assembly, this is suitably arranged in a mechanical manner, by locking. The use of screws and similar connection means is not excluded. It appears most beneficial that the first part comprises more than the connection element, i.e. also part of the—stiff—body acting as a substrate for the connection element. In one preferred embodiment, it may comprise a slot, a deformable bridge and a portion of the body. With this assembly embodiment, the first part, for instance arch-shaped, could be reused for a subsequent stage of the treatment.

According to a further aspect, the invention relates to a bracket, particularly for use in an orthodontic appliance of the invention, comprising a base for connecting the anchor to a surface of a tooth, a stem protruding from said base and a locking feature extending on the stem.

It has been found that the bracket of the present invention with its locking feature at a distance from the tooth is user-friendly and allows good cleaning. It is easier to attach or remove a connection element from the locking feature at a distance from the tooth. Moreover, the risk that a connection element would scratch against a tooth is reduced. Furthermore, when removed, a user can more easily access any space around the bracket, and therewith ensure that the tooth remains clean.

In an important embodiment hereof, the locking feature has a larger diameter than the stem, and particularly, is suitable for insertion into a slot. The insertion of the locking feature into the slot (and therewith its encapsulation) leads to a very good force transmission from said connection element via the stem to the tooth, and therewith optimizes the orthodontic treatment. Preferably, the slot is a latching slot, which fixates the locking feature once inserted. In a further embodiment, the locking feature has been configured substantially as a disc. Most suitably, the disc has an oval shape in perpendicular projection on the base. This means that the disc is elongated in an elongation direction substantially parallel to the primary axis of the tooth. Suitably the stem or a part thereof are also elongated along this primary axis of the tooth.

In again a further embodiment, a rotatable connection for rotating the locking feature relative to the base is present. This rotatable connection is suitably part of the stem. The setting of the orientation of the locking feature provides an additional degree of freedom in the orthodontic treatment. Moreover, such a rotation may be desired in the course of an orthodontic treatment as a consequence of displacement of a tooth. A rotatable connection may be beneficial so as to manufacture the bracket as much as possible from standardized elements and still allowing freedom to tune the bracket to the individual teeth and jaw of a patient.

It is foreseen that the rotatable connection is such that merely an orthodontic practitioner rather than the patient himself, could set the orientation. This may be achieved, for instance with locking means and/or by increasing the resistance against rotation such that tools are needed for such a rotation. Moreover, it is not necessary or even preferred that all brackets in a set of brackets for one patient are provided with a rotatable connection. For instance, such rotatable connection may be particularly beneficial for edge teeth. The bracket of the present invention is suitable for use in the above mentioned appliance with a directly joined connection element and body. However, the bracket may also be used advantageously in combination with more traditional appliances, such as for instance a wire member to which cooperating connection elements are coupled. It is for instance feasible that the appliance with the directly joined connection element and body would merely be applied in one or more stages of the orthodontic treatment, whereas a conventional appliance is used in other stages.

According again a further aspect, the invention relates to a component for use in an orthodontic appliance of the invention, comprising a body with at least one connection element suitable for coupling to a bracket, said connection element and said body constituting a monolithic unit.

Both the bracket and the component are particularly designed for use in accordance with preferred embodiments of the invention. The bracket is intended for use during a longer duration than the component, which is intended to be renewed for each activation stage. The component is thereto most suitably made in accordance with a process that can be specified in accordance with the forces and resulting structures needed for an orthodontic treatment.

Any embodiment and implementation discussed in relation to the appliance is also applicable to the bracket and component, where applicable, as well as to the manufacturing method and the treatment method.

BRIEF INTRODUCTION TO THE FIGURES

These and other aspects of the invention will hereinafter be elucidated with reference to the figures, which are diagrammatical and not drawn to scale, in which:

FIG. 1 schematically shows an orthodontic treatment in accordance with the prior art;

FIG. 2 schematically shows an orthodontic treatment in accordance with the invention;

FIG. 3 diagrammatically shows in a bird's eye view a tooth bracket according to a first embodiment of the invention attached to a tooth;

FIG. 4 diagrammatically shows the tooth bracket of FIG. 3 in a perspective side view;

FIG. 5 diagrammatically shows the tooth bracket of FIG. 3 in a bottom perspective view;

FIG. 6 diagrammatically shows a connection element forming part of the unit in a first embodiment in a front perspective view;

FIG. 7 diagrammatically shows the connection element of FIG. 6 in a bottom perspective view;

FIGS. 8 and 9 diagrammatically show the connection element of FIG. 6 in cross-sectional views from front and rear side;

DETAILED DISCUSSION OF ILLUSTRATED EMBODIMENTS

Figure 1:
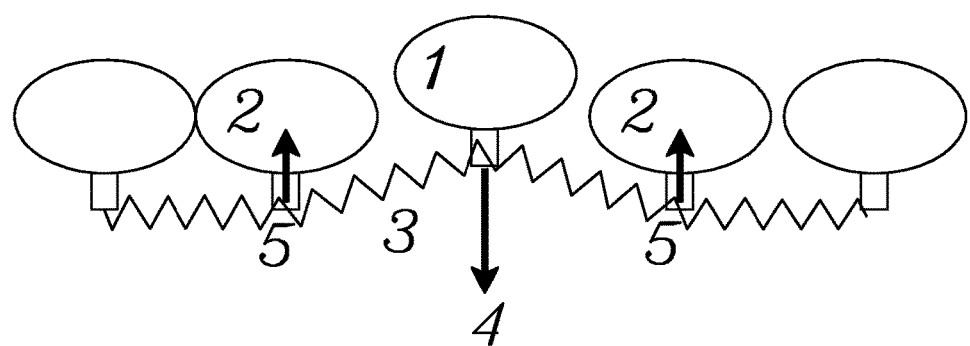

The Figures are not drawn to scale and are purely intended for illustrative purposes. Equal reference numerals in different figures refer to equal or corresponding element. FIG. 1 shows a prior art, conventional orthodontic treatment in a schematic view, making use of a flexible element 103 coupled to brackets attached to individual teeth 1, 2. The flexible element 103 is typically an archwire. Its flexibility and its specific shape depend on the material, thickness and any optional bending defined by an orthodontist for activation purposes, as known to the skilled person. The archwire is typically connected to a bracket by means of a groove in the bracket that is provided with clamps or clips or the like, so as to prevent that the archwire leaves the groove unexpectedly. The flexible element 103 generates a treatment force 4 on tooth 1. Therewith, it also generates relatively large and possibly unwanted reciprocal opposed forces 5 on adjacent teeth 2. This can result in possibly unwanted movement of adjacent teeth 2.

Figure 2:
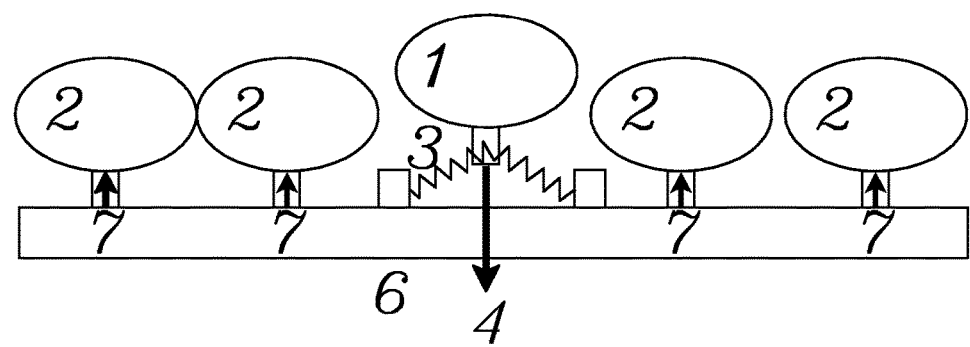

FIG. 2 shows the orthodontic treatment of the present invention in a schematic view. Herein, use is made of the orthodontic appliance of the invention, comprising a body 6 and attached thereto a local connection element 3 to a bracket. The force 4 on the tooth 1 is generated in the connection element 3, which thereto suitably comprises a structure of deformable material, also referred to as a bridge. The deformable material is less stiff than the body 6. As a result, the reactive force is spread over substantially all teeth 2, or at least a plurality of teeth 2. Due to this spreading, the resulting counterforces 7 are significantly smaller. More precisely, in one specific implementation, the treatment force applied to tooth 1 from the flexible connection element 3 results in much lower resultant forces 7 on adjacent teeth 2 thanks to the stiff removable body 6 spreading the forces over all the teeth. As a result, the risk for undesired displacement of adjacent teeth 2 is overall strongly reduced.

In this embodiment, the body 6 is shown in a strip-wise version with the connection element 3 applied on top of the strip 6. It is observed that the strip could contain a cavity or valley at the location of the connection element 3, so as to allow more space therefore, when the tooth 1 gets indeed displaced and moves towards the body 6. Preferably, as will be elucidated with reference to further figures, the connection element is designed, for deformation after that the appliance is attached to the teeth 1, 2. The deformed connection element 3, particularly a deformable bridge thereof, exerts then a force in that it would like to return to its undeformed position. In the schematic view of FIG. 2, the connection element is to be deformed—after the initial provision of the appliance by means of expansion or elongation.

It is an advantage of the method of the present invention, that the treatment is also feasible in case that two or more adjacent teeth are misaligned relative to the other teeth. The wire-based method as shown in FIG. 1 is known not to provide adequate results in such situations, since a force is applied on a tooth relative to the adjacent teeth.

The body 6 is in a preferred implementation composed of a printable material, such as a polymer. However, the body could alternatively be composed of metal, a ceramic material or a composite.

Figure 3:
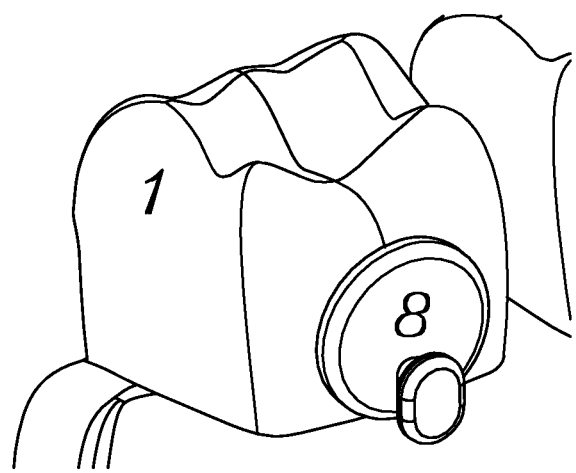
Figure 4:
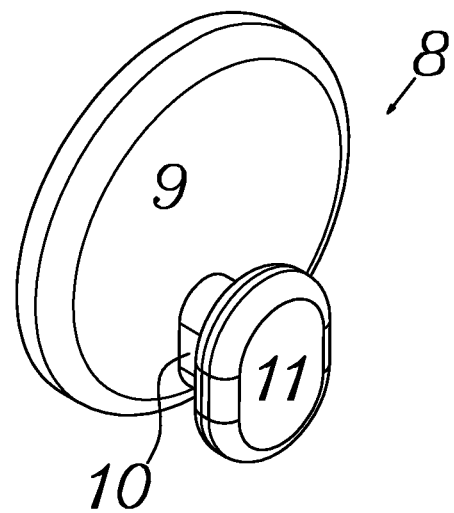
Figure 5:
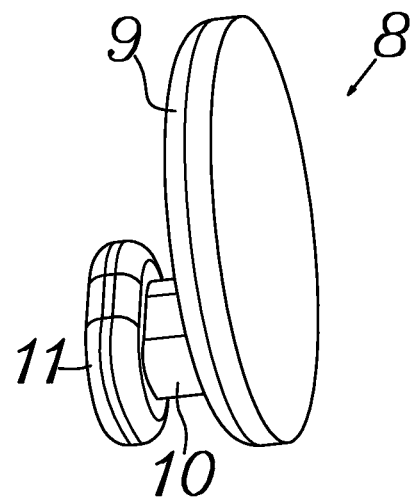

FIG. 3 shows a tooth 1 to which a tooth bracket 8 is attached. FIGS. 4 and 5 show the tooth bracket 8 in more detail and in an enlarged view. FIG. 4 shows herein a frontal side view. FIG. 5 shows the tooth bracket in a lower rear view.

The tooth 1 is shown with a first and an opposed second side face arranged in a row with the adjacent teeth. The tooth 1 is further shown to have a top face. For sake of clarity, this top face can be oriented upwards, i.e. to the top, when the appliance is used for the lower jaw/row of teeth. The top face is alternatively oriented downwards, when the appliance is used for the upper jaw/upper row of teeth. The bracket 8 is shown to the attached to one face of the tooth. This could be either the inner, lingual side of the teeth, or the outer side of the teeth that is visible from outside.

The tooth bracket 8 has a base 9 for attachment to a tooth 1 with an attaching surface 12. This attaching surface 12 is defined to match the surface of the tooth 1. Such matching can be achieved on the basis of photographs or 3D-models taken from the teeth. Typically, a bracket 8 with an appropriate attaching surface 12 may be selected from a set of standardized brackets for a specific tooth (i.e. a tooth at a specific position). Where needed, the attaching surface may be pre-treated to match the surface of the tooth 1 adequately. Attachment to the tooth will be obtained by means of a suitable adhesive. The process of applying brackets to teeth is known per se to the skilled person, so that the techniques and procedures of getting an attaching surface 12 of a bracket 8 and a tooth surface to match will be clear to a skilled person.

The bracket suitably comprises metal, ceramics or composite, though a polymer material is a feasible alternative. Composites may be beneficial in allowing a combination of sufficient strength and thickness as well as an appropriate manufacturability. Composites are known per se and comprise for instance a binder material, typically a polymer material, one or more fillers and that may be composed of inorganic material. In order to provide an optimal force transmission, it is preferred that the bracket does not comprise pores, or at least no pores of a substantial size. Ceramics are already in use for the manufacture of crowns for teeth, and have a very good fit to teeth. A preferred type of ceramics is based on zirconia.

The bracket 8 comprises, in the shown embodiment, a stem 10 protruding out of the base 9. A first locking feature 11 is provided at an end of the stem 10. This locking feature 11 is a disc-like section in the shown embodiment, which is however not essential. The disc-like section 11 suitably has a larger height than width, and preferably has a substantially oval shape. It is preferred that edges of the section 11 are rounded off, so as to reduce risk of hurting the patient and to allow an easy locking. The enlarged section 11 on the stem 10 will be hereinafter also be referred to as the "bracket protrusion".

The bracket protrusion 11 furthermore has a larger diameter than the stem 10. This allows that a complementary locking feature defined in the connection element, may encapsulate the bracket protrusion 11 on the front side and the rear side, as well as sidewise and/or at the top and the bottom. The bracket protrusion 11 suitably has a standardized design from tooth to tooth.

The stem 10 and the base 9 may be variable in shape, so as to accommodate the individual tooth, to which the bracket 8 is attached, but also in view of the exact location of the polymer body 6. In the present embodiment, the stem 10 is arranged to the base 9 outside the centre of the base 9; i.e. the central axis through the base 9 and the central axis through the stem 10 do not coincide. It is deemed beneficial, but not necessary, that the base 9 is present at a lower half of the tooth.

Figure 18:
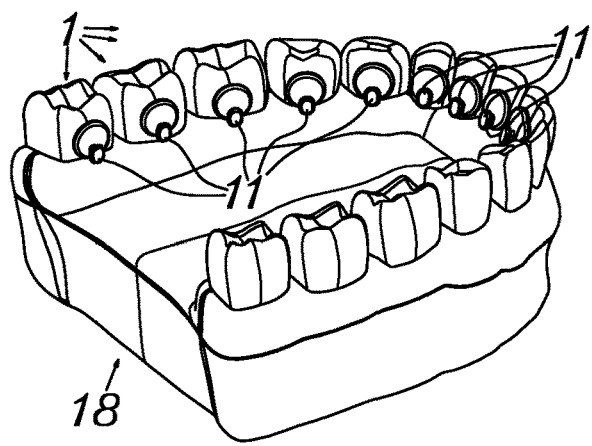
FIG. 18 shows a set of teeth with tooth brackets attached to each of the teeth.
Figure 19:
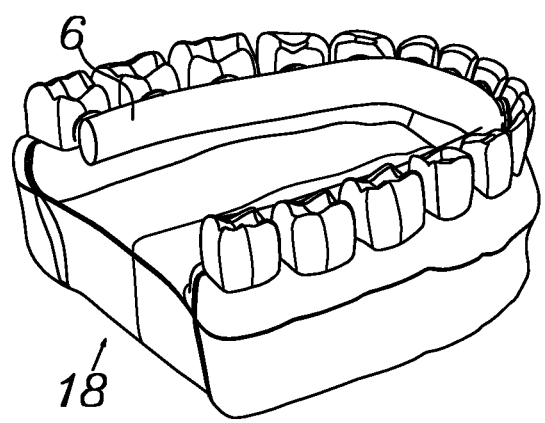
FIG. 19 shows the unit of FIG. 17 applied on the teeth with the brackets as shown in FIG. 18.

In the shown embodiment, the stem 10 has a constant width and length along its height. This is not deemed necessary. Furthermore, the transition between the base 9 and stem 10 may be gradual and may be specified to obtain maximum strength which can resist forces resulting from insertion and/or removal of the bracket protrusion 11 into and out of a slot acting as the complementary locking feature. Moreover, the shape of the stem may be varied so as to obtain sufficient ease of insertion and removal, but also to provide a correct force transmission from the connection element 3 to the tooth 1. It is also feasible that the stem 10 is provided with a longer height than minimum for insertion and removal of the bracket protrusion 11. A reason may well be that the body 6 is given an overall shifted position relative to a horizontal plane extending through a center of the row of teeth, and that the stem is used for bridging this shift at least partially, as shown in FIGS. 18 and 19.

Figure 20:
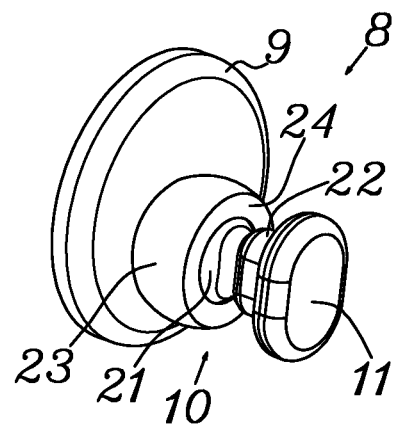
FIG. 20 shows an alternative tooth bracket with adjustable orientation between base and locking device.

FIG. 20 shows a second embodiment of a bracket according to the invention in a bird eye's perspective. The locking feature 11 can herein be oriented relative to the base 9, by means of a rotatable connection. In the shown embodiment, the rotatable connection is embodied in the stem 10, which comprises a first part 23, a second part 22 and a rotatable member 21. This configuration appears advantageous, as providing a reliable connection between the stem 10 and the base and nevertheless allowing that the locking feature 11 is insertable into a slot of a connection element. In this configuration, the rotatable member 21 is present, at least largely, within the hollow first part 23. The rotatable member 21 extends through an aperture in a top side of the first part 23, as defined by means of a ring 24, and is connected to the second part 22. However, it will be understood that the opposite, wherein the rotatable member 21 would be hidden within the second part 22 and connected to the first part 23, is a feasible alternative. Alternative configurations are however not excluded. For instance, the stem 10 may be coupled to the base 9 over a rotatable connection or the stem 10 may be coupled to the locking feature 11 over a rotatable connection. Such configurations however appear to become more bulky and less reliable.

As shown in FIG. 20, the locking feature 11 is substantially disc shaped, and in perpendicular projection onto the base 9, of substantially oval shape. The oval shape, i.e. elongated in the primary axis of the tooth, is deemed beneficial for optimum force transfer in preferably all six dimensions from the connection element to the tooth. The rounded edges facilitate insertion without a risk for hurting a user. Suitably, as shown in this FIG. 20, the second part 22 of the stem 10 and its connection to the rotatable member 21 are designed to have an elongated shape with the same direction of elongation as the locking feature 11. This is deemed beneficial both for stability reasons and for an optimum force transmission.

In the embodiment shown in FIG. 20, the rotatable member 21 is suitably configurable in any orientation. It is however not excluded, that the rotatable member 21 and the first part 23 of the stem are configured so as to have a number of predefined orientations. Such limitation of the available number of orientations could be useful to increase robustness of the stem 10.

Moreover, for robustness and or reliability, stabilisation means may be present for stabilizing a chosen orientation of the rotatable member 21. One implementation of such stabilisation means is a locking mechanism at the rear side and/or side faces of the rotatable member 21 and the inside of the first part 23. Such locking mechanism may be embodied as a lock and key. However, it is also deemed feasible that use is made of plate-like features, increasing resistance of and/or limiting movement of the rotatable member 21. Another implementation of such stabilisation means is for instance an elastically deformable mass, which adopts a shape complementary to that of the rotatable member 21, i.e. as a pillow. A further implementation may be with screws or the like, that for instance may fixate the rotatable member. Holes with screw thread may be present in the rotatable member thereto.

Furthermore, locking means may be provided, so as to ensure that merely an orthodontic practitioner is able to change the orientation of the rotatable member 21. Such locking means could lock the first part 23 or change the aperture within the ring 24, for instance by addition of a cover, rather than fixate the rotatable member 21 itself. The rotatable member 21 could further comprise an extendable portion, so as to extend a distance between locking feature 11 and base 9.

The bracket 8 as shown in FIG. 20 could be manufactured as a set of two separate elements, i.e. the base 9 plus first part 23 and the locking feature 11 plus second part 22 plus rotatable member 21. Alternatively, some of these parts may be manufactured separately and thereafter assembled together mechanically and/or chemically. The latter may be suitable from cost perspective, and so as to allow that the bracket 8 may be constructed from standardized elements as much as possible. Also, it could well be that the base, needed attachment of the tooth surface is defined in a different material that the other parts.

While it is preferable that the rotatable connection is embodied with a rotatable member 21 present in a hollow first part 23, the stem could alternatively be configured to be rotatable by virtue of its design, such that a practitioner is able to create a deformation of the stem by means of a tool, for instance tongs, such as a pair of pliers as known to the practitioner.

Figure 6:
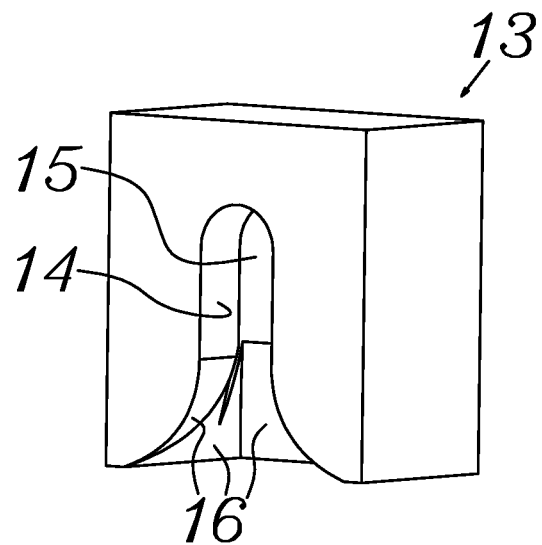
Figure 7:
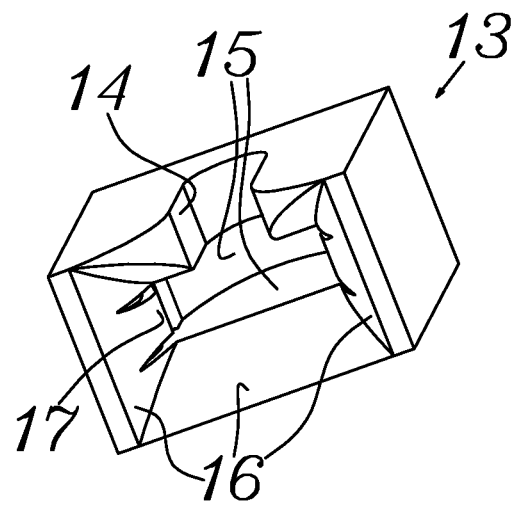
Figure 8:
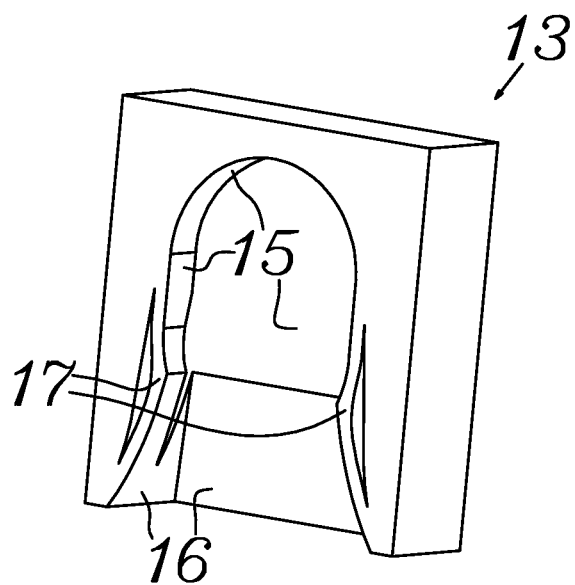
Figure 9:
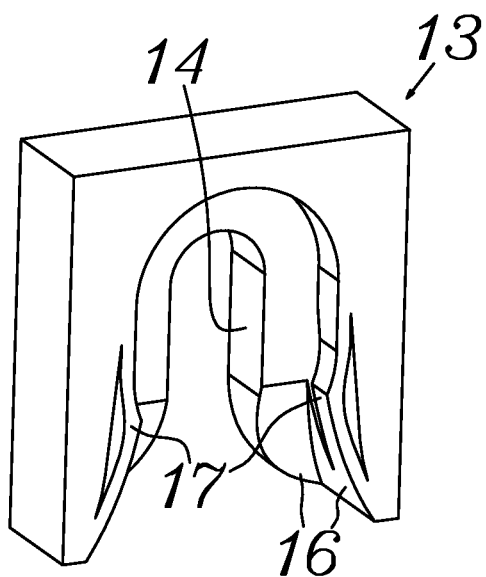

FIG. 6-9 show the locking feature 13 of the connection element in various views. FIG. 6 is a front view. FIG. 7 is a bottom view. FIG. 8 is a cross-sectional view of the rear half. FIG. 9 is a cross-sectional view of the front half. In other words, FIGS. 6 and 7 show the locking feature 13 with a cover, and FIGS. 8 and 9 without cover.

The locking feature of the present embodiment is a slot 13 designed to fit around the bracket protrusion 11. The slot 13 is provided with a primary aperture through which the bracket protrusion 11 can be inserted and removed. Most suitably, this is the lower surface of the slot 13. This surface is then opposed to the top surface of the teeth. This orientation tends to minimize the risk that food portions will enter the cavity in the slot 13. Such entry could block removal of the bracket protrusion from the slot. However, an alternative orientation is not excluded.

The slot 13 is further provided with a secondary slot aperture 14, which is designed to slide over the stem 10 of the bracket. The cavity of the slot 13 is suitably provided with mating surfaces 15 to the bracket protrusion 11, and with one or more guiding surfaces 16. Such guiding surfaces are arranged to guide a top surface of the bracket protrusion into the slot 13. They run inwards starting at a lower edge of the slot 13.

A latch 17 is present at the primary aperture, so as to prevent unintended removal of the bracket protrusion 11 from the slot 13. The latch 17 is in the shown embodiment a tip or protruding section at the interface between said one or more guiding surface 16 and said mating surface 15. During attachment, the latches of the latching slot deform so that the bracket protrusion can slide through, and spring back to their original shape to lock the bracket protrusion in place once the bracket protrusion is fully inside the latching slot. During detachment, the bracket protrusion is forced against the latches with sufficient force to open them again. The latches are sufficiently stiff to withstand forces and torques applied during tooth manipulation, but sufficiently flexible to allow detachment without hurting the patient. Other ways for releasing the bracket protrusion 11 from the slot 13 may be envisaged, for instance by means of a variation of the width of the stem, such that a rotation of the slot relatively to the bracket protrusion 11 or vice versa can release bracket protrusion 11 along the latch 17.

Most preferably, the latching slot 13 fits like a glove over the bracket protrusion 11, with mating surfaces 15 to the bracket protrusion 11 preventing relative movement in 5 degrees of freedom, and latches preventing relative movement in the only remaining 6th degree of freedom once in place.

When seen from the first aperture, the slot within the connection element may be shaped to have a diameter that reduces with increasing distance to the first aperture. The locking feature may be a shape that fits well into the slot with a small tolerance of play. The shape is suitably optimized to have sufficient resistance against movement in all directions. A disc, a pyramid or a tetragonal shape, or any combination thereof, preferably with one or more rounded edges, appear best.

Figure 10:
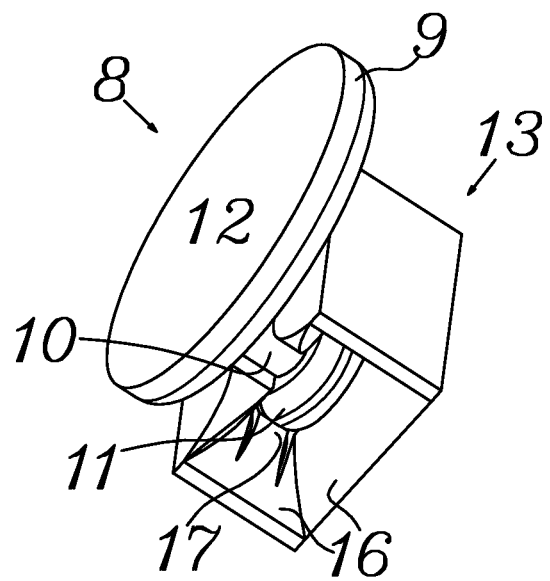
FIG. 10 shows a combination of the tooth bracket as shown in FIG. 3-5 and the connection element as shown in FIG. 6-9 in a bottom perspective view.
Figure 11:
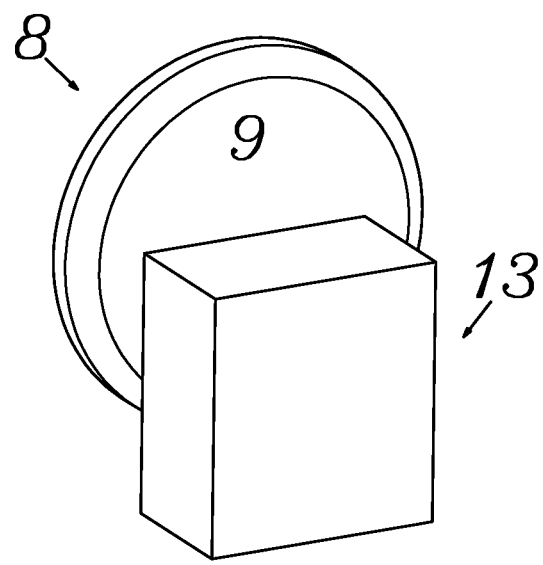
FIG. 11 shows the combination of FIG. 10 from a rear view, wherein the component is provided with a cover.

FIG. 10 and FIG. 11 show the tooth bracket 8 latched into the latching slot 13 from different angles.

Figure 12:
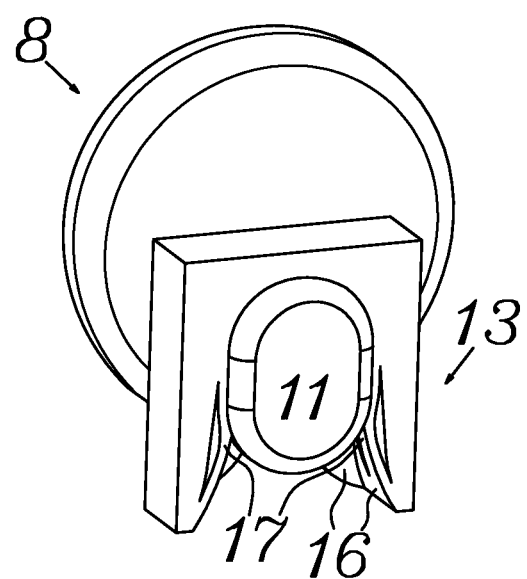
FIG. 12 shows the combination of FIG. 11 without cover.

FIG. 12 shows a cross sectional view of the tooth bracket 8 latched into the latching slot 13. Herein, the complete tooth bracket 8 and the front half of the slot 13 are shown. This view corresponds to the front half shown in FIG. 9. The figures clearly show how latch 17 locks bracket protrusion 11 in place, after that its entry has been guided by guiding surfaces 16.

Figure 13:
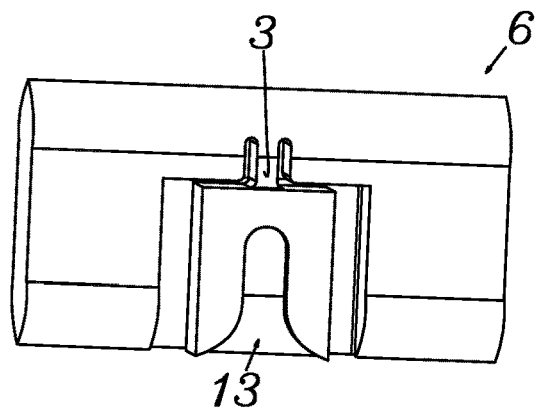
FIG. 13 shows a first embodiment of the unit of the body and the connection element in a front side view.
Figure 14:
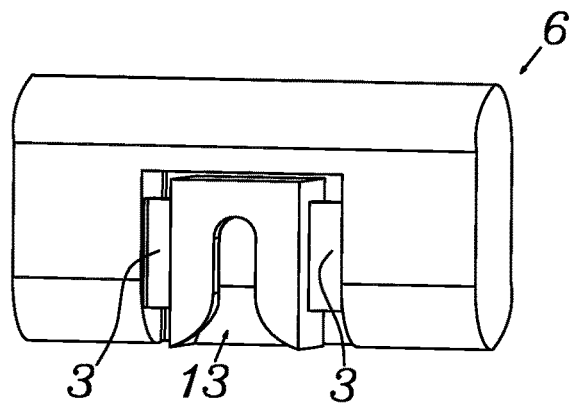
FIG. 14 shows an alternative embodiment of the unit, again in front side view.
Figure 15:
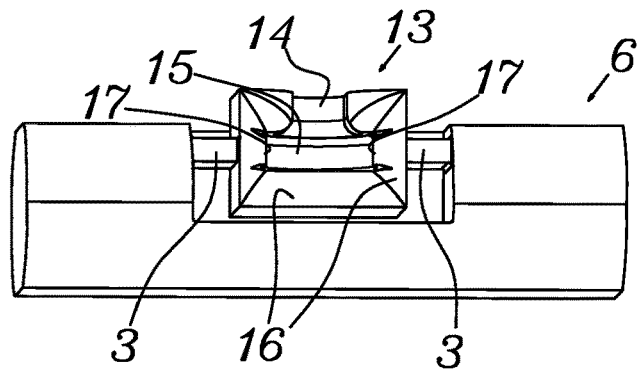
FIG. 15 shows the unit of FIG. 13 in a bottom side view.

FIG. 13-15 show in diagrammatical views the polymer body 6 onto which are arranged one or more connection elements 3. It is observed that the FIGS. 13 and 14-15 show first and second implementations, mutually differing with respect to the design of the deformable bridge. FIG. 13 shows the deformable bridge at the top side of the connection element. In FIGS. 14 and 15, the deformable bridge is shown sidewise.

The function of the deformable bridge is best explained with reference to FIGS. 14 and 15 particularly. Herein, it is shown that the deformable bridge 3 connects the slot 13 to the polymer body 6. While the FIGS. 14 & 15 suggest that the deformable bridge 3 has a straight extension, this is not necessary true. Rather, the form, material and thickness of the bridge are chosen in view of the needed force on the tooth. In correspondence with the situation shown in FIG. 2, the tooth needs to be drawn backwards. Then, the deformable bridge may be designed as a means suitable for expansion. However, other designs are not excluded. It may even be preferred with the current system, to push a tooth forward, rather than to draw it backwards.

In a preferred embodiment, the deformable bridge is deformed upon insertion of the bracket into the slot. The design of the deformable bridge is chosen, so as to get a spring-like force for returning to its undeformed state. It is this spring-like return force that will be transmitted to the respective tooth.

It is observed that the deformable bridge is shown to be much smaller than the slot itself. This is a matter of design. However, typically, the forces in orthodontic treatments are relatively small, for instance in the order of 1-2 N per tooth, such as 1.5 N.

While the FIG. 15 in particularly shows the deformable bridge 3 as a locally arranged, separate element, this is not deemed a most preferred embodiment. Alternatively, the deformable bridge is a portion of a matrix structure, wherein the chosen material(s) of the deformable bridge define the elasticity, and wherein the matrix structure ensures stability. The deformable bridge 3 is designed so as to provide a force that is preferably specified in more than one dimension, preferably at least three dimensions and more preferably, four, five or all six dimensions. It will be understood that the direction, but also the specificity of the force orientation may change in the course of an orthodontic treatment.

The deformable bridge is suitably made by means of a prototyping manufacturing technique, such as rapid prototyping, rapid manufacturing, CNC milling or layered manufactured. One specific example thereof is three-dimensional printing. This technique has the benefit that the unit may be remanufactured with amended connection elements and particularly modified deformable bridges, so as to start a subsequent stage in the orthodontic treatment. It is foreseen that the complete unit will be manufactured for each activation stage. This also has the advantage that the unit constitutes a single construction, with a minimum of deviations due to assembled links. Such manufacture could be carried out locally, in a workshop of an orthodontist, or alternatively in dedicated workshops and/or laboratories.

While it is foreseen that the manufacture may be at once, trimming areas could be built in, so that an orthodontist may make modifications if that is preferred. Such trimming areas are more particularly areas from which material could be removed or could be added. Alternatively, the trimming areas may be predefined to allow a material modification leading to revised properties. For instance a trimming area (particularly a volume) may be heated or irradiated in a predefined manner to achieve cross-linking of a polymer material, therewith reducing the elasticity. Alternatively, the trimming area may be an empty volume, for instance a cavity, which can be filled with a dedicated material.

An important part of such rapid prototyping manufacturing technique is the preceding step, wherein the body to be manufactured is defined in a computer system, on the basis of an input. The use of scanning techniques is known in the field of dentistry and orthodontics, as an aid for providing accurate treatments. One such method is for instance known from WO2011/067510 that is included herein by reference.

A specific step in a manufacturing method of the appliance, and particularly the body therein, is the determination of the forces to be applied, and the resulting derivation of a design of a connection element and any deformable bridges therein.

This method has several advantages over a conventional method of orthodontic treatment. First of all, the conversion of a scanned image to a design of a connection element is feasible with a significantly higher resolution. Secondly, the progress of the orthodontic treatment may be followed, in that scans from different moments may be compared. Since the applied forces are known with a high precision, expectations may be made on the further progress, and about any undesired side effects. This allows to optimize a treatment. Furthermore, the specific tools allow a comparison with other patients, i.e. other treatments carried out separately. This comparison is suitably made via a database, which may be built up on the basis of treatments and designs.

A further advantage of such method is that it will be based on scans, such as of X-ray, CB-CT, MRI. This allows to identify not only a malocclusion or other artefacts on the basis of the positioning of the teeth, but also the underlying root. Since a tooth and its root form are coexistent, the treatment may be more effective.

Typically, the manufacturing may thus be subdivided in the following steps.

In a first step, the positions of the teeth, suitably with their underlying roots, are identified with an analysis technique.

In a second step, such positions are mutually compared and desired adaptation to arrive at a better positioning is defined. The adaptation is suitably defined in six dimensions.

In a third step, a treatment plan is defined, in which the desired adaptation is subdivided into several stages, each requiring a separate activation, i.e. different forces to be applied.

In a fourth step, the forces to be applied in one or more activation stages are calculated. These forces will be calculated in a plurality of dimensions. Furthermore, a duration of the force will be identified.

In a fifth step, a structure will be defined on the basis of the defined force. Suitably, use is made of a library of predefined, parametric, structures available in a memory of a computer system, so as to choose one structure. A predefined structure may have been designed in terms of size, material, shape, density, optionally porosity, and optionally the number of substructures needed. For instance, in FIG. 15, the deformed bridge comprises at least a first and a second substructure on opposite sides of the connection element. Herewith the design is effectively complete and manufacture may be carried out. This design will be stored. Preferably, the results of preceding steps are stored as well. It will be understood that the design may be prepared with the support of one or more computer programs.

It is added for sake of clarity, that this method may be split between various professionals acting in the field of orthodontics and appliance manufacturing or dentistry laboratory. For instance, the treatment plan could be defined by an orthodontic practitioner, whereas one or more of the other steps are carried out by technically qualified personnel without involvement of the orthodontic practitioner.

The manufacture suitably comprises a rapid prototyping technique. The manufacturing may contain several steps, and also a manufacturing plan. For instance, the manufacturing plan could include a review step, whether a manufacturing apparatus is suitable for defining the desired structure. If not, either the structure could be modified, or a suitable manufacturing apparatus, and/or a manufacturing sequence can be defined. Further review steps as to the availability of needed manufacturing materials may be included.

Optionally, a post-treatment step may be carried out in the manufacture, such as for instance on the basis of the above mentioned trimming areas.

The invention therefore also relates to a computer based design method for at least one connection element of an orthodontic appliance, which connection element is most suitably arranged on a body. The connection element typically comprises a deformable bridge between a locking feature such as a slot and the polymer body. Said design method is based on a 3D orthodontic treatment plan that is provided in electronic form, and that comprises digital representations of actual and desired positions of one or more teeth of a patient according to one or more, typically a plurality of activation stages. This method comprises the steps of:

Loading the 3D orthodontic treatment plan into a computer;

Calculating a needed force on a teeth for an activation stage of the 3D orthodontic treatment plan, said force calculation optionally including a tolerance margin calculation Defining a design for a connection element on the basis of the needed force on a respective tooth;

Storing the design in a memory.

Preferably, the design is herein calculated by means of (1) accessing a database; (2) comparing the needed force and tolerance margin if any with predefined design templates for a specific tooth, force and tolerance margin if any available in the database; (3) choosing at least one suitable design template; (4) specifying the design on the basis of the chosen design template.

Optionally, the design definition may include a review step as to whether the specified design is manufacturable on the basis of the available manufacturing means, and if not a step for redesigning the design.

Suitably, the design definition comprises the step of combining several connection elements with a body to arrive at a design of a unit.

Furthermore, the design, particularly that of the complete unit may include specific signs into a surface. Such signs can improve user friendliness, definition of centre, top side and/or bottom side. The signs may further be used to specify an identifier. Such identifier may also contain a version number. The signs may further contain any personalized or desired statements. The design is suitably made in the course of the manufacturing process, such that no additional material is needed. Any such additional material may dissolve in the conditions applicable in the mouth, and therefore should meet highest requirements with respect to toxicity, safety and health. However, such signs may also be added after the initial manufacturing in any known technique, such as by means of printing, writing, laser processing or the like.

Use may be made in the design of software tools such as a virtual articulator.

Optionally, the forces may have been calculated separately, and merely the calculated forces are loaded into the computer.

The invention further relates to a computer based design system for such connection element.

The invention also relates to a computer supporting manufacturing method and a computer system therefore.

The invention further relates to a computer program product that when executed on a processing engine executes any of the foregoing method steps, and suitably all identified method steps.

The invention also relates to a non-transitory, machine readable storage medium storing the computer program product of the invention.

Figure 16:
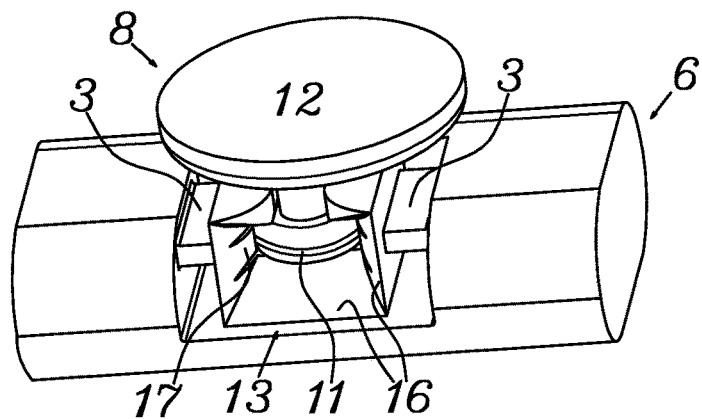
FIG. 16 shows a combination of the tooth bracket of FIG. 3-5 and the unit of FIGS. 13 and 15.

FIG. 16 shows a bottom view of latching slot 13 integrated as part of orthodontic bridge 6, with tooth bracket 8 latched into latching slot 13. There are a lot of similarities with FIG. 10. Clear to see is how guiding surfaces 16 would help guide bracket protrusion 11 during insertion, and how latches 17 keep the bracket protrusion 11 in place once inserted. Flexible elements 3 deform during insertion and provide the treatment force.

Figure 17:
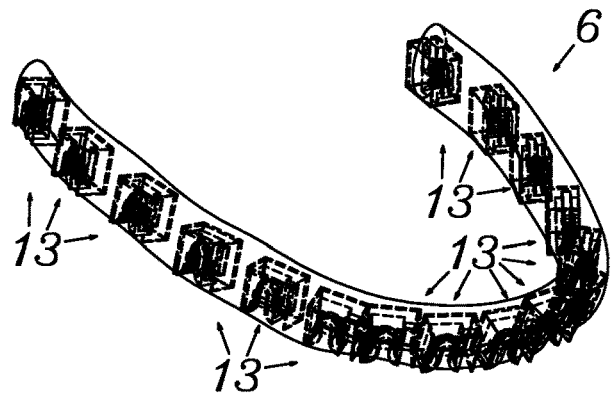
FIG. 17 shows a unit of the invention provided with a plurality of connection elements.

FIG. 17 shows a view of the complete detachable orthodontic bridge 6, with many latching slots 13 as integrated elements. This Figure illustrates the idea behind one important embodiment of the invention, that the slots of the connection elements have all substantially the same orientation, i.e. the first apertures through which the locking elements are to be entered are all on the same side. It is only upon insertion that the shape of the bridge to the connection element creates an elastic force by means of deformation. This idea is desired such that a patient may remove and enter the body with the connection elements by himself, i.e. daily without need to consult a dentist or orthodontic practitioner. More specifically, thereto the brackets or at least some of those are thereto in a preferred embodiment of the invention provided to have rotatable stem, i.e. a stem of which the orientation can be defined by an orthodontic practitioner.

FIG. 18 shows tooth brackets 8 attached to teeth 1, in preparation for treatment using orthodontic bridge 6. Latching slots 13 integrated into bridge 6 will slide over bracket protrusions 11.

FIG. 19 shows a lower jaw 13 with teeth 1, to which tooth brackets 2 are attached, over which the detachable orthodontic bridge 12 is fitted for treatment. Although current drawing shows the lower draw with bridge on the lingual side, the present invention can also be applied to the upper jaw, and labial side of both upper and lower jaw.

In summary, according to a preferred embodiment, the invention proposes an appliance comprising a body that snaps onto the brackets attached to teeth with latching slots and so becomes detachable for daily cleaning by the patient. Inside the polymeric body there is an integrated spring function. The fabrication of the polymeric body can be done by 3D printing, which makes it possible to print integrated spring elements connecting the latching slots with the body.

The invention claimed is:

1. An orthodontic appliance comprising:
a plurality of brackets, each bracket having a base for connection to a surface of a tooth within a row of teeth; and
a body configured to be coupled to each of said brackets, the body being provided with a plurality of connection elements arranged on the body, each connection element being configured to cooperate with a respective one of the plurality of brackets to form a connection between the body and the respective bracket,
wherein each connection element comprises a slot,
wherein each bracket comprises a locking element and a stem protruding from the base to connect the locking element to the base, the locking element being configured to be inserted into the slot of a respective connection element, the locking element being substantially disc-shaped and elongated in a primary axis of the respective tooth and having a larger diameter than the stem,
wherein the locking elements of the plurality of brackets and the slots of the plurality of connection elements define locking means for removably connecting the body to the plurality of brackets via the plurality of connection elements,
wherein the slot of each connection element is configured to fit around the locking element of the respective bracket, the slot comprising mating surfaces configured to form a mating engagement with the locking element of the respective bracket and at least one guiding surface configured to guide a top surface of the locking element into the slot, said at least one guiding surface running inward starting at a lower edge of the slot, the slot being a latching slot comprising a tip or protruding section at an interface between said at least one guiding surface and said mating surfaces,
wherein each connection element further comprises a first aperture through which the locking element of the respective bracket can be inserted into the slot and a second aperture configured to slide over the stem of the respective bracket,
wherein the stems of the plurality of brackets are configured so that a distance between the body and the row of teeth is sufficient for insertion and removal of the body and for cleaning of the brackets,
wherein the stem of each of the plurality of brackets is arranged on the base outside of a center of the base and a central axis of the stem is shifted with respect to a central axis of the base such that the stem is configured to define a position of the body that is shifted along the primary axis of the respective tooth with respect to a plane extending perpendicular to the primary axis of the respective tooth and through a center of the row of teeth.

2. The orthodontic appliance as claimed in claim 1, wherein each connection element comprises a deformable bridge connecting the connection element to the body, the deformable bridge being configured to deform upon connection of the respective bracket to the connection element to generate a force on the respective tooth.

3. The orthodontic appliance as claimed in claim 1, wherein the locking element of each bracket has a substantially oval shape.

4. The orthodontic appliance as claimed in claim 1, wherein the stem of each bracket is rotatably connected to the base with a rotatable connection.

5. The orthodontic appliance as claimed in claim 4, wherein the rotatable connection is configured to be rotatable prior to application of the orthodontic appliance to a patient and set after application of the orthodontic appliance to the patient.

6. The orthodontic appliance as claimed in claim 4, wherein the rotatable connection comprises a rotatable member present in a hollow first part.

7. The orthodontic appliance as claimed in claim 4, wherein the stem of each bracket is configured such that rotation of the stem causes deformation of the stem.

8. The orthodontic appliance as claimed in claim 1, wherein each of the plurality of brackets is made of at least one material different from those of the respective connection element.

9. The orthodontic appliance as claimed in claim 1, wherein each of the plurality of brackets comprises a material chosen from metal, ceramics and composite.

10. The orthodontic appliance as claimed in claim 9, wherein the material is a ceramic material based on zirconia.

11. The orthodontic appliance as claimed in claim 1, wherein the body is substantially arch-shaped.

12. The orthodontic appliance as claimed in claim 11, wherein the body is defined for insertion at the lingual side of the teeth.

13. The orthodontic appliance as claimed in claim 1, wherein the body and the plurality of connection elements constitute a monolithic unit.

14. The orthodontic appliance as claimed in claim 1, wherein the body with the plurality of connection elements is obtained by assembly of a first part and a second part with a design complementary to the first part.

15. The orthodontic appliance as claimed in claim 1, wherein the body is a polymeric body.

16. The orthodontic appliance as claimed in claim 15, wherein a surface of the body is provided with a printed visible or tactile sign.

17. The orthodontic appliance as claimed in claim 1, wherein the plurality of brackets number fewer than a number of teeth in the row of teeth of a patient receiving the orthodontic appliance.

18. The orthodontic appliance as claimed in claim 1, wherein the locking element of each of the plurality of brackets is centered on the stem.

19. The orthodontic appliance as claimed in claim 1, wherein the locking element of each of the plurality of brackets extends substantially parallel to the primary axis of the tooth.

* * * * *